(12) United States Patent
Damaser et al.

(10) Patent No.: US 12,156,746 B2
(45) Date of Patent: Dec. 3, 2024

(54) SENSING DEVICE FOR AMBULATORY URODYNAMICS HAVING A PRESSURE SENSITIVE HOUSING

(71) Applicants: THE CLEVELAND CLINIC FOUNDATION, Cleveland, OH (US); PARKER HANNIFIN CORPORATION, Cleveland, OH (US); THE UNITED STATES GOVERNMENT AS REPRESENTED BY THE DEPARTMENT OF VETERANS AFFAIRS, Washington, DC (US)

(72) Inventors: Margot S. Damaser, Cleveland, OH (US); Steve Majerus, Washington, DC (US); Hui Zhu, Cleveland, OH (US); Bradley C. Gill, Cleveland, OH (US); Ricardo Gonzalez, Cleveland, OH (US); Daniel Greene, Cleveland, OH (US); Joe Poliquin, Cleveland, OH (US); Glenn Craig, Cleveland, OH (US); Marie Lorentz, Cleveland, OH (US); Gino Banco, Cleveland, OH (US)

(73) Assignees: THE CLEVELAND CLINIC FOUNDATION, Cleveland, OH (US); THE UNITED STATES GOVERNMENT AS REPRESENTED BY THE DEPARTMENT OF VETERANS AFFAIRS, Washington, DC (US); PARKER HANNIFIN CORPORATION, Cleveland, OH (US)

( * ) Notice: Subject to any disclaimer, the term of this patent is extended or adjusted under 35 U.S.C. 154(b) by 610 days.

(21) Appl. No.: 17/058,783

(22) PCT Filed: May 28, 2019

(86) PCT No.: PCT/US2019/034123
§ 371 (c)(1),
(2) Date: Nov. 25, 2020

(87) PCT Pub. No.: WO2019/227092
PCT Pub. Date: Nov. 28, 2019

(65) Prior Publication Data
US 2021/0196203 A1 Jul. 1, 2021

Related U.S. Application Data

(60) Provisional application No. 62/676,361, filed on May 25, 2018.

(51) Int. Cl.
*A61B 5/00* (2006.01)
*A61B 5/0538* (2021.01)
(Continued)

(52) U.S. Cl.
CPC .......... *A61B 5/6874* (2013.01); *A61B 5/0538* (2013.01); *A61B 5/07* (2013.01);
(Continued)

(58) Field of Classification Search
None
See application file for complete search history.

(56) References Cited

U.S. PATENT DOCUMENTS

2003/0100839 A1* 5/2003 Cohen .................... A61B 5/389
600/486
2003/0229263 A1* 12/2003 Connors ................. A61F 2/004
600/29

(Continued)

FOREIGN PATENT DOCUMENTS

JP 2002369810 A 12/2002
KR 20120016442 A * 8/2010 ............. A61B 5/205

(Continued)

OTHER PUBLICATIONS

Translation of KR20120016442A. Retrieved Apr. 19, 2023 (Year: 2023).*

(Continued)

*Primary Examiner* — Benjamin S Melhus
*Assistant Examiner* — Samuel C Kim
(74) *Attorney, Agent, or Firm* — Tarolli, Sundheim, Covell & Tummino LLP

(57) ABSTRACT

A sensing device can be used for ambulatory urodynamics. The sensing device can include an elongated outer housing constructed of flexible material that can curve within a patient's bladder. At least a portion of the outer housing can be filled with a non-compressible fluid. A flexible printed circuit board can be disposed within the outer housing to curve with the outer housing. The printed circuit board can include a pressure sensor, comprising a diaphragm, to collect pressure data; a microcontroller running control software; and a wireless transmitter to transmit the pressure data. A battery can be disposed within the outer housing and coupled to the printed circuit board. The flexible material of the outer housing is configured to be displaced by a pressure within the patient's bladder, the displacement is transmitted through the non-compressible fluid to the pressure sensor that provides the pressure data based on the displacement.

19 Claims, 8 Drawing Sheets

(51) Int. Cl.
  *A61B 5/07* (2006.01)
  *A61B 5/20* (2006.01)
(52) U.S. Cl.
  CPC .............. *A61B 5/204* (2013.01); *A61B 5/205* (2013.01); *A61B 2560/0209* (2013.01); *A61B 2560/066* (2013.01); *A61B 2562/0247* (2013.01); *A61B 2562/06* (2013.01); *A61B 2562/164* (2013.01); *A61B 2562/166* (2013.01); *A61B 2562/168* (2013.01)

(56) References Cited

U.S. PATENT DOCUMENTS

| | | | |
|---|---|---|---|
| 2005/0177067 A1* | 8/2005 | Tracey | A61B 5/208 128/903 |
| 2006/0247723 A1 | 11/2006 | Gerber | |
| 2015/0164401 A1* | 6/2015 | Toth | A61B 5/1459 606/41 |
| 2015/0223745 A1 | 8/2015 | Wille | |
| 2015/0305671 A1* | 10/2015 | Yoon | A61B 5/01 600/28 |
| 2016/0374576 A1* | 12/2016 | Ziaie | A61B 5/205 600/561 |
| 2018/0199816 A1* | 7/2018 | Kalt | A61B 5/204 |

FOREIGN PATENT DOCUMENTS

| | | | | |
|---|---|---|---|---|
| WO | WO-2005115245 A1 * | 12/2005 | ........... | A61B 5/1076 |
| WO | 2016191479 A1 | 12/2016 | | |
| WO | 2017136212 A1 | 8/2017 | | |

OTHER PUBLICATIONS

T. J. Coleman et al., "A Gel filled intravaginal transducer for extended measurements of intra-abdominal pressure," 2010 Annual International Conference of the IEEE Engineering in Medicine and Biology, Buenos Aires, Argentina, 2010, pp. 1852-1855, doi: 10.1109/IEMBS.2010.5625987. (Year: 2010).*
PCT International Search Report and Written Opinion for corresponding International Application Serial No. PCT/US2019/034123, mailed Aug. 16, 2019, pp. 1-18.
European Office Action dated Apr. 26, 2023, pp. 1-6.
Kim et al.: "A generic packaging technique using fluidic isolation for low-drift implantable pressure sensors", 2015 Transducers—2015 18th International Conference on Solid-State Sensors, Actuators and Microsystems, IEEE, Jun. 21, 2015, pp. 476-479.

* cited by examiner

SENSING DEVICE FOR AMBULATORY URODYNAMICS HAVING A PRESSURE SENSITIVE HOUSING

CROSS-REFERENCE TO RELATED APPLICATIONS

This application is a national phase application of and claims priority from PCT International Patent Application PCT/US19/34123, filed May 28, 2019, which claims the benefit of U.S. Provisional Application No. 62/676,361, filed May 25, 2018, entitled "NON-SURGICAL MECHANISMS FOR AMBULATORY URODYNAMICS". The subject matter of each of the aforementioned applications is hereby incorporated by reference in its entirety.

TECHNICAL FIELD

The present disclosure relates generally to ambulatory urodynamics and, more specifically, to a sensing device that can be used for ambulatory urodynamics having a pressure sensitive housing.

BACKGROUND

Disorders of the lower urinary tract (LUT) are prevalent in men and women and are characterized by symptoms like increased urinary frequency, nocturia, urinary urgency, and urinary incontinence. Currently, LUT disorders are diagnosed with a battery of laboratory-based urodynamic tests, which typically require insertion of catheters both transuretherally and either transvaginally or transrectally. Patients are then required to void while the catheters are inserted and in the presence of laboratory personnel. Consequently, laboratory-based urodynamics may result in pain, discomfort, anxiety, and embarrassment for patients. In addition, laboratory-based urodynamics may be unreliable, with high rates of false negatives and false positives, due to the unnatural, forced voiding.

Ambulatory urodynamics systems, in contrast, remove the use of uncomfortable catheters, eliminate the artificial laboratory environment, and allow for assessment of bladder function during normal activity. However, current ambulatory urodynamics systems require the use of either sensors that are implanted in the bladder, resulting in significantly increased testing costs and a prolonged patient recovery period prior to device usage, or externally worn sensors, which may result in patient noncompliance.

SUMMARY

The present disclosure relates to a sensing device that can be used for ambulatory urodynamics. The sensing device reduces the need for using sensors that are implanted in the bladder, and externally worn sensors, resulting in lower testing costs and better patient compliance.

In an aspect, the present disclosure describes a sensing device. The sensing device includes an elongated outer housing constructed of flexible material to be configured to curve within a patient's bladder. At least a portion of the elongated outer housing is filled with a non-compressible fluid. The sensing device also includes a flexible printed circuit board disposed within the elongated outer housing and configured to curve with the outer housing. The flexible printed circuit board can include a pressure sensor, comprising a diaphragm, to collect pressure data; a microcontroller running control software; and a wireless transmitter to transmit the pressure data. The sensing device can also include a battery disposed within the outer housing and coupled to the printed circuit board to power at least one of the pressure sensor, the microcontroller, and the wireless transmitter. The flexible material of the elongated outer housing can be displaced by a pressure within the patient's bladder, the displacement of the flexible material of the elongated outer housing is transmitted through the non-compressible fluid to the pressure sensor that detects the displacement and provides the pressure data based on the displacement.

In another aspect, the present disclosure describes a method for sensing bladder pressure. The method includes deforming a portion of a flexible material of an elongated outer housing of a sensing device by a pressure within a patient's bladder. The sensing device includes the elongated outer housing constructed of the flexible material to be configured to curve within a patient's bladder, at least a portion of the elongated outer housing is filled with a non-compressible fluid; a flexible printed circuit board disposed within the elongated outer housing and configured to curve with the outer housing (including a pressure sensor, comprising a diaphragm, to collect pressure data; a microcontroller running control software; and a wireless transmitter to transmit the pressure data), and a battery disposed within the outer housing and coupled to the printed circuit board to power at least one of the pressure sensor, the microcontroller, and the wireless transmitter. The method also includes transmitting the displacement of the flexible material of the outer housing through the non-compressible fluid to the pressure sensor and detecting, by the pressure sensor, the displacement to provide the pressure data based on the displacement.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
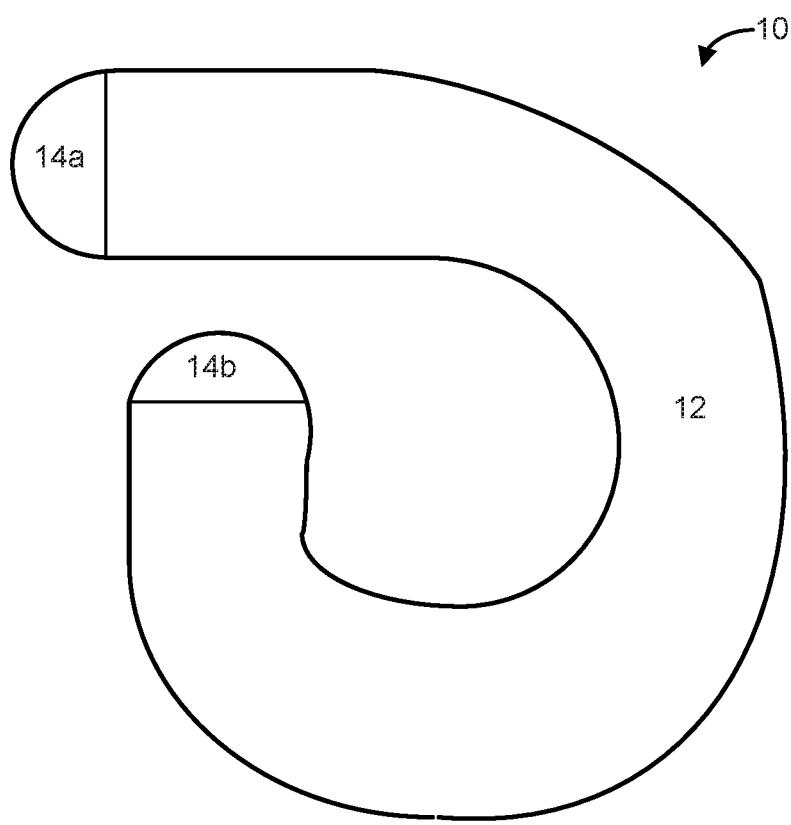
FIG. 1 illustrates a diagram of an exterior view of a portion of a sensing device that can be used for ambulatory urodynamics having a pressure sensitive housing, according to an aspect of the present disclosure.

In the context of the present disclosure, the singular forms "a," "an" and "the" can also include the plural forms, unless the context clearly indicates otherwise.

As used herein, the terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "bladder" can refer to the "urinary bladder", a hollow organ that collects urine before disposal by urination. The bladder can exhibit a bladder volume and a bladder pressure, which can be measured.

As used herein, the term "urodynamics" can refer to a study assessing how the bladder and urethra are performing their job of storing and releasing urine.

As used herein, the term "ambulatory urodynamics" can refer to any functional test of the lower urinary tract predominantly utilizing natural filling of the bladder. Ambulatory urodynamics is different from conventional urodynamics, which uses artificial, non-physiological filling of the bladder and/or voiding.

As used herein, the term "self-coiling" can refer to a function of an object automatically curling or assuming a circular or semicircular shape upon being released from being held in a linear position by another object.

As used herein, the term "sensing device" can refer to any device with one or more components (e.g., sensors and/or transducers) that detect or measure one or more physical properties and one or more components that record, indicate, or otherwise respond to the one or more physical properties. A "uromonitor" is an example of a sensing device.

As used herein, the term "subject" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to ambulatory urodynamics. Although superior to laboratory-based urodynamics, current ambulatory urodynamics require either surgical implementation of transducers into the bladder, resulting in significantly increased testing costs and a prolonged patient recovery period prior to device usage, or externally worn sensors, which may result in patient noncompliance. The present disclosure reduces the expense and increases patient compliance by providing a single sensing device that can detect bladder pressure. The single sensing device, in some examples, can also detect volume of the bladder.

The single sensing device includes an elongated outer housing made of a flexible material and at least a portion filled with a non-compressible material. The flexible material can be displaced by a pressure within the patient's bladder; the displacement of the flexible material can be transmitted through the non-compressible fluid to a pressure sensor on a flexible circuit board within the outer housing. The pressure sensor can detect the displacement and provides the pressure data based on the displacement. Advantageously, using the flexible material and the non-compressible material in this manner can increase the pressure sensing ability and/or resolution of the sensing device so that external sensors are not expressly necessary.

III. Systems

Figure 2:
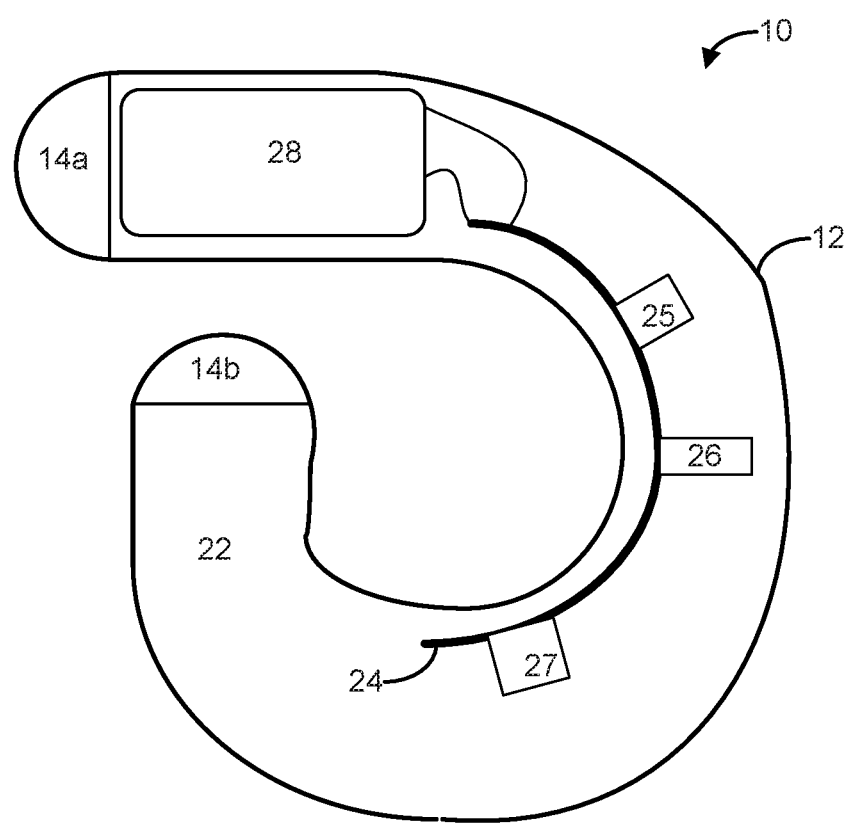
FIG. 2 illustrates a diagram of an interior view of the sensing device of FIG. 1.

FIGS. 1 and 2 together illustrate a sensing device 10 that can be used for ambulatory urodynamics. While ambulatory urodynamics generally reduces the pain, discomfort, anxiety, and embarrassment characteristic of traditional urodynamics, disadvantages of ambulatory urodynamics include an added expense and a lack of patient compliance due to requirement of one or more externally worn and/or surgically implanted sensors/transducers. The sensing device 10 overcomes these disadvantages by eliminating the requirement of additional sensors and/or transducers.

FIG. 1 shows an exterior view of the sensing device 10. The exterior of the sensing device 10 includes an elongated outer housing 12 constructed of a flexible material, which still protects the interior of the sensing device 10 from the environment within the bladder (e.g., urine). The flexible material can be one or more biocompatible rubbers, like polyurethane, polyisoprene, silicone, ethylene propylene diene terpolymer (EPDM), and the like. The flexible material can be configured to curve (or self-coil) within a patient's bladder. In some instances, the sensing device 10 can also include one or more end portions 14a, 14b. The end portions 14a, 14b can be shaped in any manner that facilitates removal of the sensing device 10 from the patient's bladder. As illustrated in FIG. 1, the end portions 14a, 14b can have a semi-circular form, which may decrease damage to the bladder in the event the sensing device 10 contacts the bladder. Additionally, one or more of the end portions 14a, 14b can have a suture hole through which a removal facilitation device (like a string) can be attached. The end portions 14a, 14b can also help to secure components within the outer housing 12.

FIG. 2 shows an interior view of the sensing device 10. At least a portion of the outer housing 12 can be filled with a non-compressible fluid 22. In some instances, at least 50% of the outer housing 12 can be filled with the non-compressible fluid 22. In other instances, at least 75% of the outer housing 12 can be filled with the non-compressible fluid 22. In further instances, at least 90% of the outer housing 12 can be filled with the non-compressible fluid 22. In other instances, at least 95% of the outer housing 12 can be filled with the non-compressible fluid 22. In further instances, the entirety of the outer housing 12 can be filled with the non-compressible fluid 22. The non-compressible fluid can include an electrically non-conductive material, such as silicone, a hydrogel, or the like.

A flexible printed circuit board (PCB) 24 can be disposed within the outer housing 12. In some instances, at least a portion of the PCT can covered with the non-compressible fluid. The flexible PCB 24 can be constructed of a substrate material that is configured to curve as the outer housing 12 curves. The flexible printed circuit board 24 can include a pressure sensor 25, comprising a diaphragm, to collect pressure data (or multiple similarly-configured pressure sensors); a microcontroller 26 running control software (e.g., including a microprocessor to execute software and/or a non-transitory memory to store data and software); and a wireless transmitter 27 to transmit the pressure data. In some instances, a surface of the flexible printed circuit board without (or opposite) the pressure sensor, the microcontroller, and the wireless transmitter can be disposed against an inner surface of the elongated outer housing. However, the pressure sensor 25, the microcontroller 26, and the wireless transmitter 27 (e.g., that uses radio waves to send data to and receive data from a receiver outside the patient's body) can be mounted in any position on the PCB 24 and the PCB 24 can be located at any orientation within the outer housing 12.

A battery 28 can be coupled to the PCB 24 and disposed within the outer housing 12. The battery 28 can be electrically connected to the PCB 24 to provide power to at least one of the pressure sensor 25, microcontroller 26, and the wireless transmitter 27. In one example, in order to conserve the battery 28, the sensing device 10 utilizes a two-stage wakeup process for turning on and supplying power to the sensing device 10 from the battery 28. During shelf life of the sensing device 10, while the sensing device 10 is still contained within a sterile package, for example, the sensing device 10 remains in an extremely low power mode (or a deep sleep) in which the sensing device 10 does not power up the wireless transmitter 27 or the microcontroller 26 of the PCB 24. Rather, the PCB 24 can include an inductive circuit element (not shown) which is used to power up the wireless transmitter 27 and the microcontroller 26. Specifically, the sensing device 10 begins to power up into a first stage low power mode when the inductive circuit element captures an externally supplied strong magnetic field pulse. This can be done, for example, at a supply chain level such as when the sensing device 10 is sent to a hospital or other end user. Alternatively, the sensing device 10 can be activated at the hospital or by a user (e.g., a doctor, a nurse, a technician, or other end user). Thus, the sensing device 10 consumes virtually no current while still inside the sterile packaging and waiting to be shipped to a hospital or to be used at a hospital. In one example, if the sensing device 10 is powered up to a first stage of low power mode but not immediately used, the sensing device may return to the deep sleep mode.

In the first stage low power mode, the main processor and the radio remain in sleep mode and therefore the sensing device 10 is not yet capable of processing, storing and transmitting pressure data. In order to activate such functionality, the sensing device 10 must first be awoken into full power mode, also referred to as the second stage of the two-stage wakeup process. In order to facilitate the second stage of the two-stage wakeup process, the PCB 24 can include a pressure sensor co-processor (not shown) that is configured to consume a very small amount of current and to measure pressure even while the microcontroller 26 and wireless transmitter 27 of the PCB 24 are in sleep mode. In particular, the sensor co-processor can be configured to detect pressure at the pressure sensor over a specific predefined threshold. Thus, the sensor co-processor may detect bladder contractions even as the main processor and radio remain in sleep mode. When the bladder contracts though and causes pressure to rise above the predefined threshold, the co-processor may cause the activation of the sensing device 10 and, in response to the activation, wake the sensing device 10 into a full power mode, thereby causing the main processor and radio to wake up and begin to draw current from the battery 28. Once in full power mode, the main processor may begin to process, store, and transmit pressure data. For example, a large pressure exerted on the sensing device 10 during insertion of the sensing device 10 may serve as a trigger for the sensing device 10 to wake up automatically. The two-stage wakeup process described may minimize the amount of power required from the battery 28 and therefore, reduce the necessary size of the battery 28, thereby enabling further miniaturization of the sensing device 10.

The configuration of the sensing device 10 (with the flexible outer housing 12 and the non-compressible fluid (or gel) 22 within the flexible outer housing 12) can increase the pressure sensing ability of the sensing device 10 compared to traditional devices used for ambulatory urodynamics. The entire flexible outer housing 12 of the sensing device 10 can be pressure sensitive. In other words, the entire surface area of the flexible material of the elongated outer housing can be displaceable in response to a pressure within the patient's bladder. In one example, the outer housing 12 may include additional features (not shown) designed to enhance the surface area, such as one or more dimples, ridges, grooves, or the like. The displacement of the flexible material of the elongated outer housing can be transmitted through the non-compressible fluid to the pressure sensor on the PCB 24. The pressure sensor can detect the displacement and provide the pressure data based on the displacement, thereby increasing the detection ability of the pressure sensor. The pressure sensor can leverage the entire surface area of the flexible outer housing 12 to detect the pressure within the bladder, providing a robust pressure sensing mechanism (providing stable sensing, even within the bladder) that eliminates the need for additional sensors/transducers, both externally worn and surgically implanted. The sensing device 10 is advantageous over conventional pressure sensors, which use a locally placed diaphragm or conduit in fluid connection with a diaphragm, but within a rigid housing that cannot be displaced by an applied pressure, so that the pressure sensing ability is limited to only deformation of the diaphragm itself-leading to lower sensing resolution.

Additional components related to sensing, data processing, power control, and the like, can be within or on the outer housing 12 of the sensing device 10. One example is a volume sensing unit, a part of which can be disposed on the outer housing 12 of the sensing device 10 and coupled to the PCB 24, wherein the other sensor is configured to detect bladder volume. For example, the volume sensing unit can include one or more sensors (e.g., volume sensing electrodes) to detect a property related to volume (e.g., electrical conductance, which can be correlated to bladder volume). The one or more sensors can be spaced along the outer housing 12 in any way to facilitates detection and/or correlation of the property related to volume. The number of the one or more sensors can be selected according to factors, such as patient height, weight, age, etc.

Figure 3:
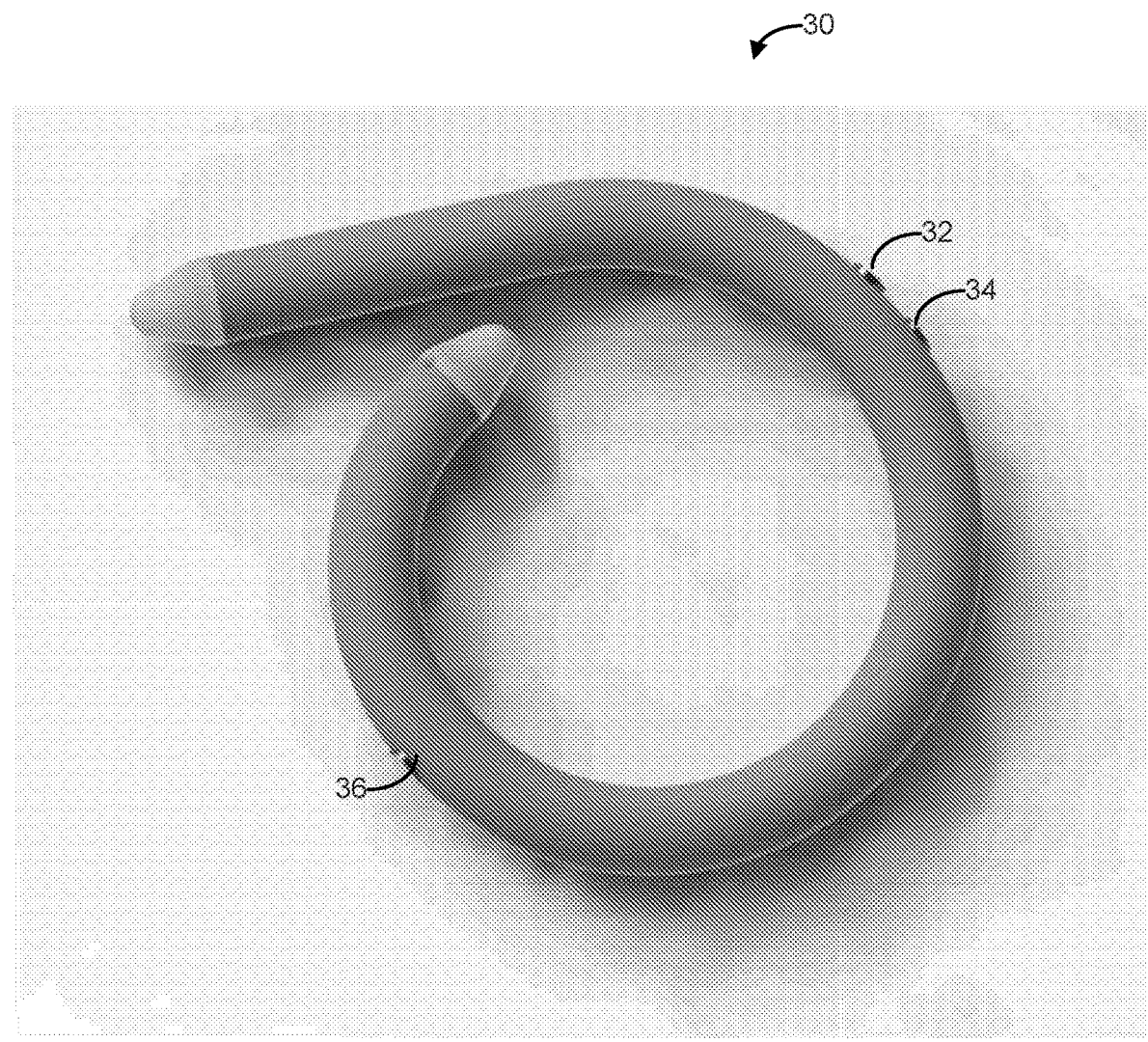
FIG. 3 illustrates an exterior view of an example sensing device that can sense pressure and volume of a patient's bladder.
Figure 4:
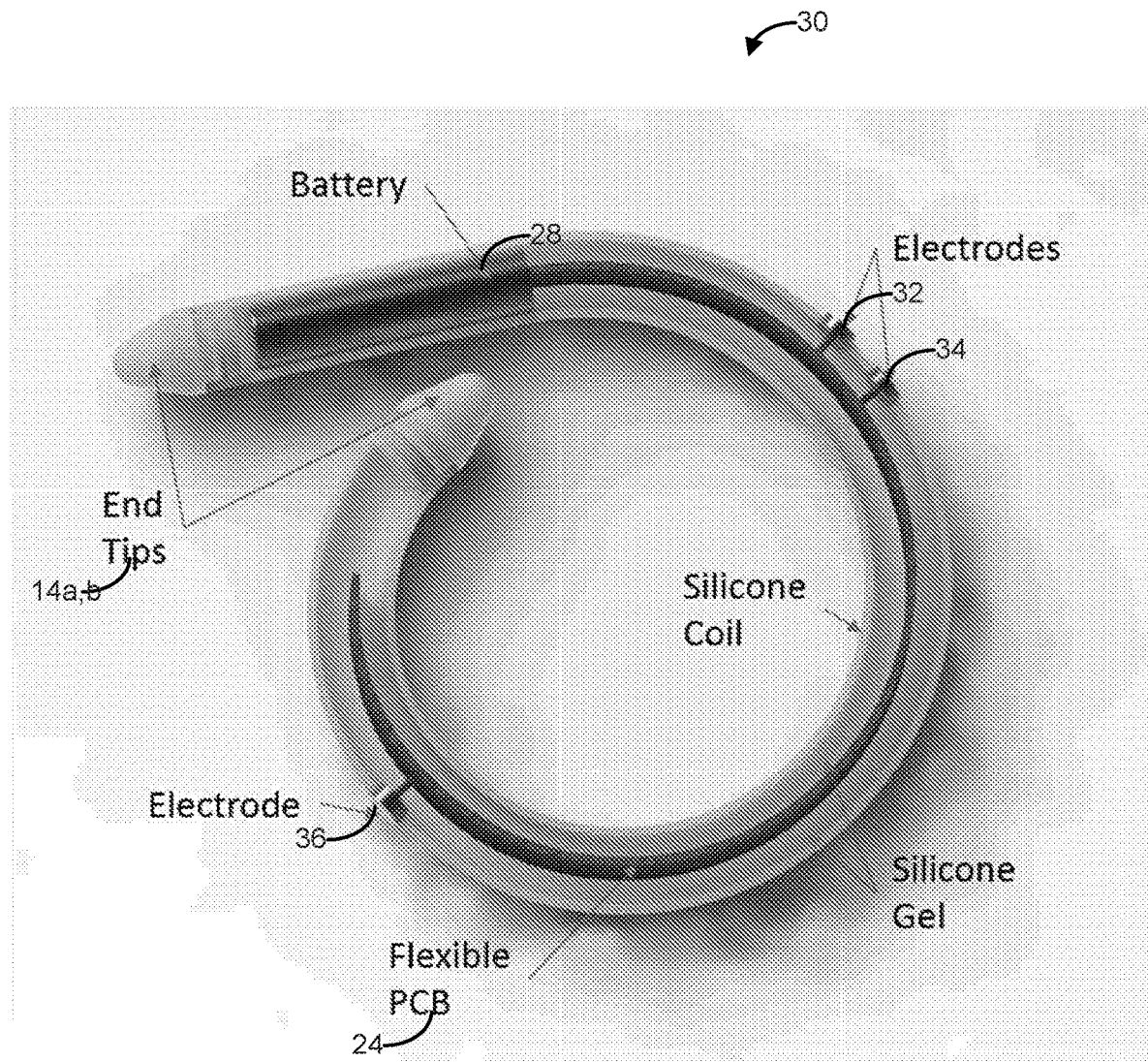
FIG. 4 illustrates an interior view of the example sensing device of FIG. 3.

As shown in FIGS. 3 and 4, the sensing device 30 uses silicone as the material of the outer housing and the interior is filled with a non-compressible silicone gel. In the example shown in FIGS. 3 and 4, the sensing device 30 can include three volume sensing electrodes 32, 34, 36 on the outer surface, and the three volume sensing electrodes extend through the housing to the PCB 24. It should be noted that the other elements of the PCB are not shown/visible in FIG. 4.

As an example, the sensing device 30 can measure volume based on electrical conductance and a mathematical equation (executed by a processor within the microcontroller) to convert the electrical conductance into bladder volume. The sensing device 30 also adjusts for different concentrations of urine with a conductivity electrode. For example, the sensing device 30 can include two probes (conductivity and conductance), seven electrodes (each probe can include two excitation electrodes and at least one voltage measurement electrode) and a ground electrode can be shared between the two probes. Accordingly, the sensing device 30 is capable of measuring bladder volume while positioned within the bladder lumen and immersed in urine, thus eliminating the need for externally worn elements for obtaining the measurements.

Figure 5:
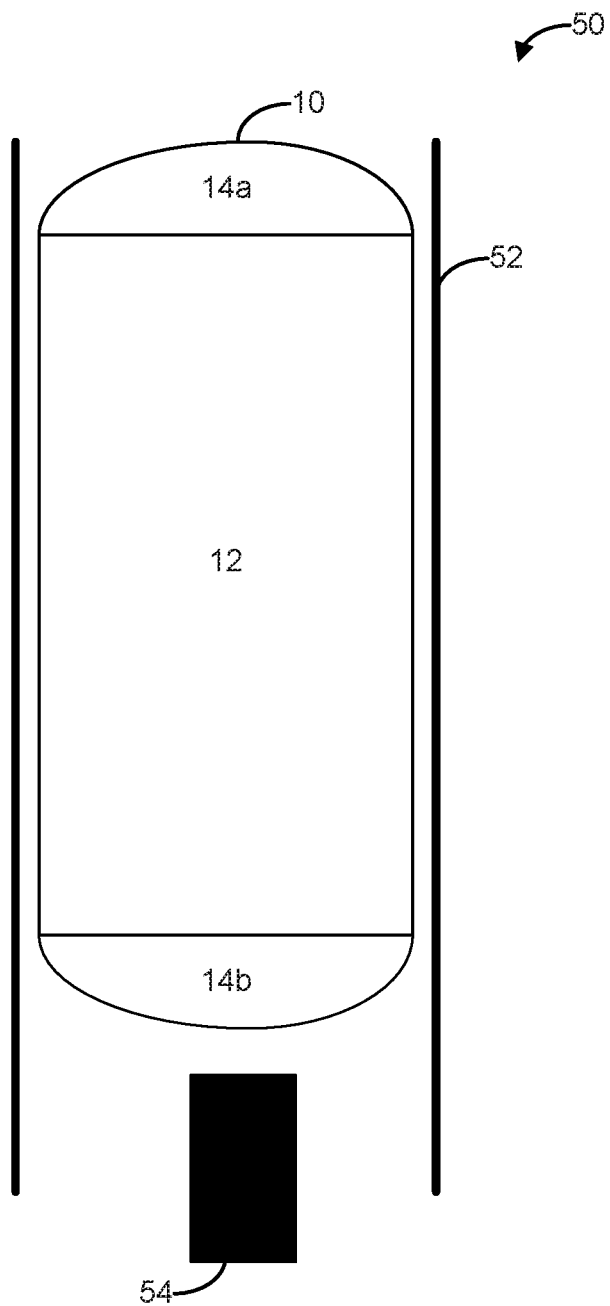
FIG. 5 illustrates a diagram of a system that can be used to deliver the sensor device of FIG. 1 into a patient's bladder.

A system 50 to deliver the sensing device 10 into a patient's bladder is shown in FIG. 5. The system 50 includes a catheter 52 and a pusher device 54. The catheter 52 may partially or completely encapsulate the sensing device 10 during delivery. The pusher device 54 can use mechanical force to push the sensing device 10 through the catheter 52 and into the bladder. In some instances, the pusher device 54 can include a handle or mechanism that can allow a user to control the application of the mechanical force to the sensing device 10. In one example, the catheter 52 can be made of medical grade silicone and the pusher device 54 can be a stainless steel coiled spring. However, the catheter 52 and/or the pusher device 54 can be made of a different material.

The catheter 52 restricts the sensing device 10 to a straight shape during delivery. Once the sensing device 10 is ejected from the catheter 52, the sensing device 10 assumes its natural curved shape, thereby assuming a smaller space within the bladder while still maintaining the same overall surface area. As shown in FIGS. 1 and 2, the sensing device 10 can be shaped in a curved shape (e.g., a coiled shape, a c-shape, a heart shape, an s-shape, or the like) within the bladder. The sensing device 10 can have a straight shape (e.g., with no curvature or with a small amount of curvature) during delivery (e.g., by the system 50) and removal (e.g., by a mechanical means, like a string attached to a suture hole on one of the ends 14*a,b*) from the bladder. The sensing device 10 can self-coil from the straight shape (e.g., a forced shape) to the curved shape (e.g., a natural or resting shape) when released into the patient's bladder.

In some instances, the catheter 52 can include one or more channels that serve to reduce internal drag as the pusher device 54 is pushed through the catheter 52. In one example, the channels also provide an opening for receiving a guide wire (not shown) that can be used to help navigate a urethra if needed. In another example, the channels provide a pathway for urine to flow past the pusher device 54, so the user can determine if the catheter 52 has been pushed fully into the bladder. As an example, the pusher device 54 can hold the sensing device 10 in position as the catheter is retracted (e.g., by staying in a position as the catheter 52 moves out of the patient's bladder).

Figure 6:
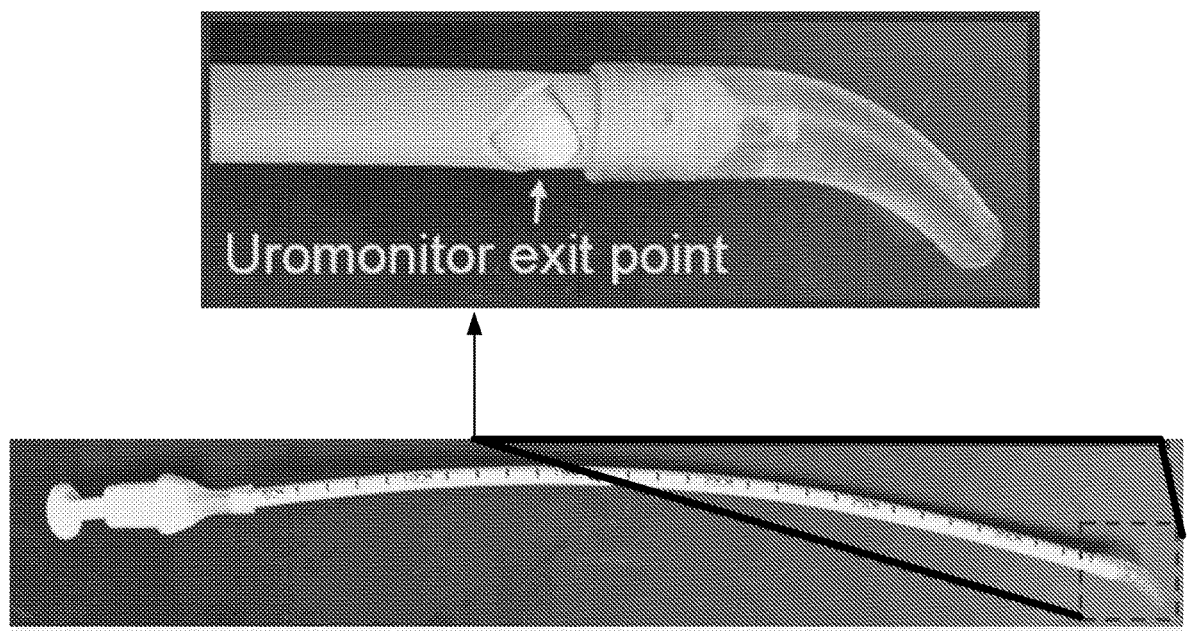
FIG. 6 is a photograph of an example of the system of FIG. 5.

The system 50 can include a male version and a female version. The male version, for example, can include a coude tip to help navigate past the male prostate during delivery of the sensing device 10. An example of the male version of the system 50 is shown in FIG. 6, including the catheter, the pushing device, and the coude tip. The "uromonitor exit point" is a point on the catheter where the sensing device 12 can exit the catheter. A specific female version does not require the coude tip.

IV. Methods

Figure 7:
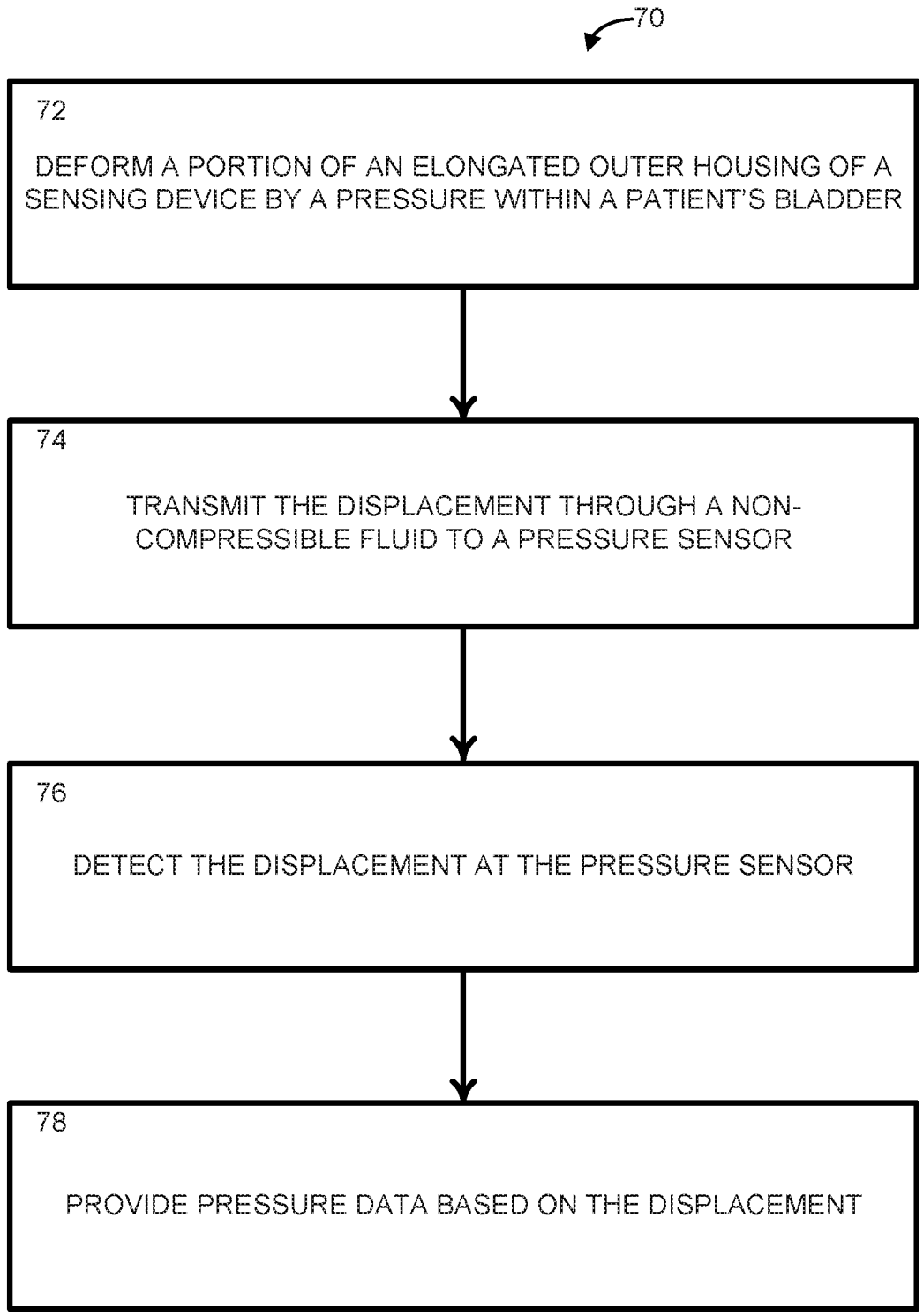
FIG. 7 illustrates a method for detecting pressure within a patient's bladder using a single sensing device, according to another aspect of the present disclosure
Figure 8:
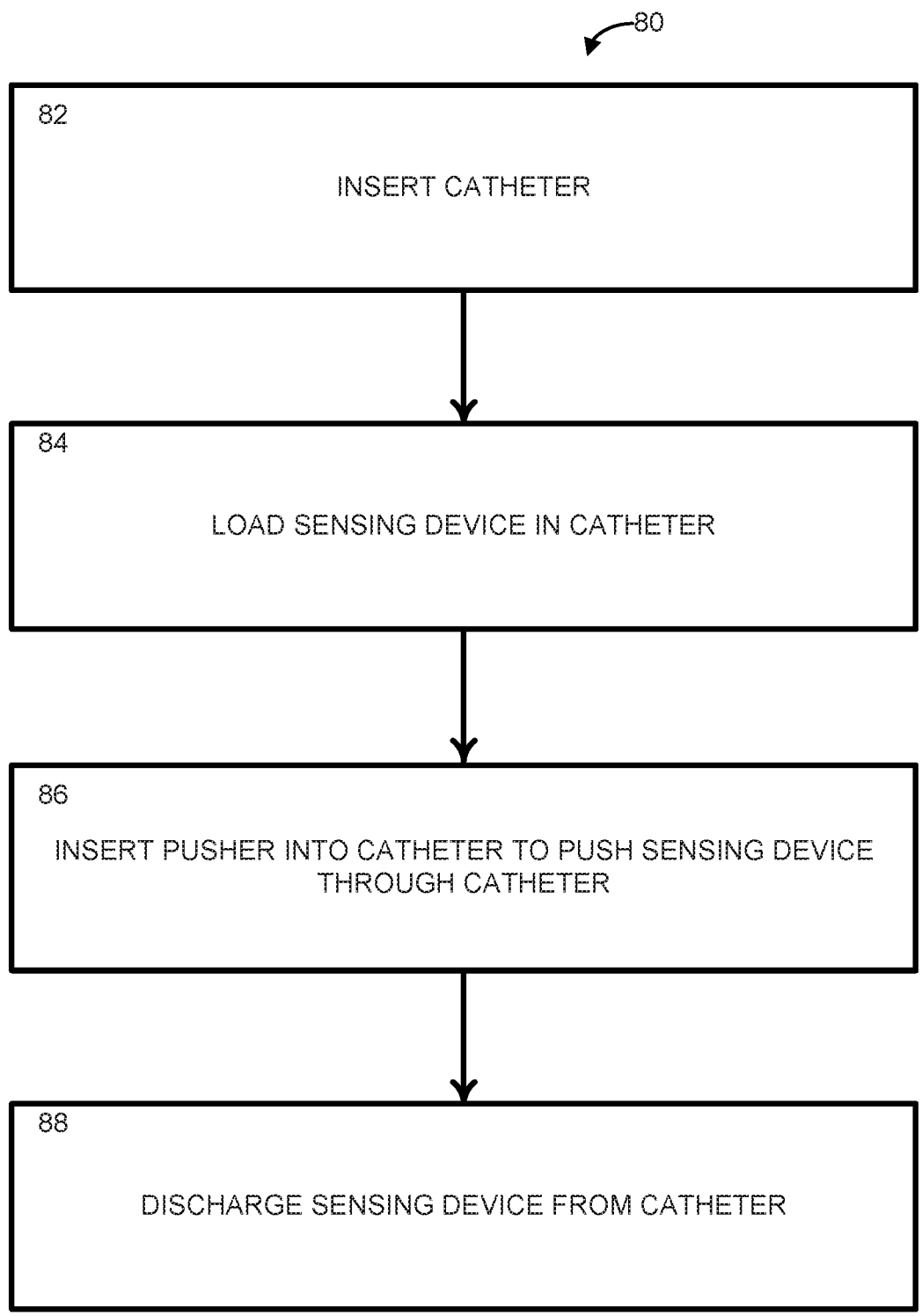
FIG. 8 illustrates a method for delivering a sensing device to a patient's bladder, according to another aspect of the present disclosure.

Another aspect of the present disclosure includes methods 70 and 80, shown in FIGS. 7 and 8, which can contribute to improved ambulatory urodynamics. For purposes of simplicity, the methods 70 and 80 are shown and described as being executed serially; however, it is to be understood that the present disclosure is not limited by the illustrated order as some steps could occur in different orders and/or concurrently with other steps shown and described herein. Moreover, not all illustrated aspects may be required to implement the methods 70 and 80.

Referring now to FIG. 7, illustrated is a method 70 for detecting pressure within a patient's bladder using a single sensing device (e.g., sensing device 10). At 72, a portion of a flexible material of an elongated outer housing of the sensing device can be deformed by a pressure within a patient's bladder. At 74, the displacement of the flexible material of the outer housing can be transmitted through the non-compressible fluid to the pressure sensor. At 76, the pressure sensor can detect the displacement. At 78, the pressure sensor can provide the pressure data (e.g., to a non-transitory memory and/or to a wireless transceiver) based on the displacement.

Shown in FIG. 8 is a method 80 for delivering a sensing device to a patient's bladder. The method 80 can be executed using the system 50, for example. At 82, a catheter (e.g., catheter 52) can be inserted into a patient's urethra and guided to a patient's bladder. A first end of the catheter is external to the patient's body, while the second end of the catheter can be guided to the patient's bladder. In one example, a guide wire can be inserted into a channel of the catheter to help guide the catheter into and/or through the urethra. At 84, the sensing device (e.g., sensing device 10) can be loaded into the catheter. The sensing device can be inserted through the first end of the catheter either before or after the second end of the catheter has reached the urethra. At 86, a pusher (e.g., pusher device 54) can be inserted into the first end of the catheter. The pusher can use a mechanical mechanism (e.g., pressure by pushing) to aid the sensing device through the catheter and into the patient's bladder. Alternatively, the sensing device and/or the pusher can be pre-loaded into the catheter. At 88, the sensing device can be discharged or pushed out from the catheter and into the patient's urethra and/or bladder. Alternatively, the pusher can be held in place and the catheter can be retracted. The sensing device can change from a forced-straight position to a natural curved position upon discharging from the catheter.

V. Example Use

The sensing device 10 can be used to provide a non-surgical mechanism for ambulatory urodynamics. The sensing device 10 can be inserted into a bladder through the patient's urethra using a delivery system (e.g., according to the method of FIG. 8, using the systems shown in FIGS. 5-6). The delivery system can deliver the sensing device 10 through the patient's urethra, moving the sensing device 10 from a position external to the patient's body into the patient's bladder without requiring a surgical procedure. Once positioned inside the patient's bladder (e.g., free floating within the patient's bladder), the sensing device enables data collection in a more cost effective manner while reducing patient pain, anxiety, embarrassment, as well as non-compliance. Since the sensing device 10 can collect pressure data from any direction (e.g., pressure can exert a force on any portion of the outer housing 12 of the sensing device 10), the sensing device 10 may be positioned according to any orientation inside the bladder without affecting the accuracy or effectiveness of the sensing device 10. When the ambulatory urodynamics test is complete, the sensing device 10 can be removed from the patient's bladder manually (e.g., by pulling a string attached to the sensing device and extending through the urethra). The flexible outer housing 12 and the flexible printed circuit board 24 allow the sensing device 10 to be delivered through the urethra, curve in the patient's bladder when free of the urethra (to prevent expelling from the bladder during urination), and straighten when pulled through the urethra to exit the patent's bladder.

From the above description, those skilled in the art will perceive improvements, changes and modifications. Such improvements, changes and modifications are within the skill of one in the art and are intended to be covered by the appended claims.

What is claimed is:

1. A sensing device configured to free float within a patient's bladder, the sensing device comprising:
    an elongated outer housing constructed entirely of flexible material and configured to curve within the patient's bladder, wherein the elongated outer housing comprises an interior filled with a volume of a non-compressible fluid, wherein the elongated outer housing is further configured to deform in response to a bladder pressure and to displace the volume of the non-compressible fluid within the interior of the elongated outer housing, wherein the elongated outer housing further comprises a first end and a second end opposite the first end, wherein a first end tip is secured to the first end of the elongated outer housing and a second end tip is secured to the second end of the elongated outer housing and the first and second end tips are configured to seal the volume of the non-compressible fluid within the interior of the elongated outer housing;
    a flexible printed circuit board encapsulated within the interior of the elongated outer housing and configured to curve with the outer housing, the flexible printed circuit board comprising:
        a pressure sensor, comprising a diaphragm, configured to detect displacement of the volume of the non-compressible fluid in the interior of the elongated outer housing in response to the bladder pressure deforming the elongated outer housing and to collect pressure data based on the displacement of the volume of the non-compressible fluid;
        a microcontroller configured to run control software; and
        a wireless transmitter configured to transmit the pressure data;
    a battery encapsulated within the interior of the elongated outer housing and positioned proximate the first end of the elongated housing, wherein the flexible printed circuit board is coupled to the battery and extends from the battery through the interior of the elongated outer housing towards the second end of the elongated outer housing, wherein the battery is configured to power at least one of the pressure sensor, the microcontroller, and the wireless transmitter,
        wherein the pressure sensor is positioned more proximate the battery than the microcontroller and the wireless transmitter,
        wherein the sensing device is configured to conserve power delivered from the battery with a low power mode and a full power mode; and
    a pressure sensor co-processor configured to detect pressure at the pressure sensor that is over a predefined threshold when the sensing device is in the low power mode and to activate the sensing device to the full power mode when an insertion pressure is detected,
        wherein the sensing device is configured to experience the displacement of the volume of the non-compressible fluid in response to the bladder pressure in any direction.

2. The sensing device of claim 1, wherein the flexible material of the elongated outer housing comprises a biocompatible rubber and the non-compressible fluid comprises an electrically non-conductive material.

3. The sensing device of claim 2, wherein the biocompatible rubber comprises at least one of polyurethane, polyisoprene, silicone, and ethylene propylene diene terpolymer (EPDM).

4. The sensing device of claim 2, wherein the electrically non-conductive material comprises at least one of silicone or a hydrogel.

5. The sensing device of claim 1, wherein a surface of the flexible printed circuit board without the pressure sensor, the microcontroller, and the wireless transmitter is disposed against a surface of the interior of the elongated outer housing.

6. The sensing device of claim 1, further comprising a second sensor disposed on the elongated outer housing and coupled to the flexible printed circuit board, wherein the second sensor is configured to detect bladder volume.

7. The sensing device of claim 6, wherein the second sensor detects an electrical conductance within the patient's bladder, wherein the electrical conductance correlates to the bladder volume.

8. The sensing device of claim 1, wherein the sensing device is configured to be delivered into the patient's bladder through a catheter using a pusher device.

9. The sensing device of claim 1, further comprising a string that facilitates removal of the sensing device from the patient's bladder.

10. A method comprising:
    inserting a sensing device in a low power conservation mode into a patient's bladder, wherein the sensing device comprises a pressure sensor co-processor configured to detect pressure on the sensing device and to activate the sensing device to a full power mode when an insertion pressure is detected;
    triggering the sensing device to activate to the full power mode;
    deforming a portion of a flexible material of an elongated outer housing of the sensing device by a pressure within the patient's bladder,
    wherein the sensing device is configured to free float within the patient's bladder and further comprises:
        the elongated outer housing constructed entirely of the flexible material configured to curve within the patient's bladder, wherein at least a portion of the elongated outer housing is filled with a volume of a non-compressible fluid, wherein deforming the portion of the flexible material displaces the volume of the non-compressible fluid within the elongated outer housing,
        wherein the elongated outer housing further comprises a first end and a second end opposite the first end, wherein a first end tip is secured to the first end of the elongated outer housing and a second end tip is secured to the second end of the elongated outer housing and the first and second end tips are configured to seal the volume of the non-compressible fluid within an interior of the elongated outer housing;
        a flexible printed circuit board disposed within the elongated outer housing and configured to curve with the outer housing, the flexible printed circuit board comprising:
            a pressure sensor comprising a diaphragm;
            a microcontroller configured to run control software; and a wireless transmitter configured to transmit the pressure data; and a battery disposed within the outer housing and coupled to the printed circuit board to power at least one of the pressure sensor, the microcontroller, and the wireless transmitter;

transmitting forces associated with the deformation of the flexible material of the outer housing through the non-compressible fluid to the pressure sensor;

detecting, by the pressure sensor, the displacement of the volume of the non-compressible fluid in the elongated outer housing in response to the pressure within the patient's bladder; and determining, by the pressure sensor, pressure data based on the detected displacement of the volume of the non-compressible fluid in the elongated outer housing.

11. The method of claim 10, wherein the sensing device is straight during insertion and curves into a curved shape after insertion.

12. The method of claim 11, wherein the curved shape comprises a coiled shape, a c-shape, a heart shape, or an s-shape.

13. The method of claim 10, wherein the inserting comprises:

inserting a catheter into a urethra of the patient and guiding the catheter to the patient's bladder;

inserting the sensing device into the catheter;

pushing the sensing device through the catheter towards the patient's bladder with a pushing device; and discharging the sensing device via an opening in the catheter into the bladder.

14. The method of claim 13, wherein the pushing device includes a handle to aid in the pushing the sensing device through the catheter.

15. The method of claim 10, further comprising removing the sensing device from the bladder by pulling a string attached to the sensing device and extending through a urethra of the patient.

16. The method of claim 10, further comprising detecting, by another sensor within the sensing device, an electrical conductance within the patient's bladder, wherein the electrical conductance correlates to the bladder volume.

17. The method of claim 10, wherein the flexible material of the elongated outer housing comprises a biocompatible rubber and the non-compressible fluid comprises an electrically non-conductive material.

18. The method of claim 17, wherein the biocompatible rubber comprises at least one of polyurethane, polyisoprene, silicone, and ethylene propylene diene terpolymer (EPDM).

19. The method of claim 17, wherein the electrically non-conductive material comprises at least one of silicone or a hydrogel.

* * * * *